(12) United States Patent
Sabel et al.

(10) Patent No.: US 7,402,573 B2
(45) Date of Patent: Jul. 22, 2008

(54) USE OF NANOPARTICLES FOR THE DNA ADMINISTRATION TO A TARGET ORGAN

(75) Inventors: Bernhard Sabel, Berlin (DE); Christian Walz, Magdeburg (DE); Kerstin Ringe, Magdeburg (DE)

(73) Assignee: NanoDel Technologies GmbH, Magdeburg (DE)

( * ) Notice: Subject to any disclaimer, the term of this patent is extended or adjusted under 35 U.S.C. 154(b) by 347 days.

(21) Appl. No.: 11/041,606

(22) Filed: Jan. 24, 2005

(65) Prior Publication Data
US 2005/0175710 A1    Aug. 11, 2005

Related U.S. Application Data

(63) Continuation of application No. PCT/EP02/08434, filed on Jul. 29, 2002.

(51) Int. Cl.
*A61K 31/713* (2006.01)
(52) U.S. Cl. .......................................... 514/44; 435/459
(58) Field of Classification Search ....................... None
See application file for complete search history.

(56) References Cited

U.S. PATENT DOCUMENTS 6,248,720 B1    6/2001  Mathiowitz et al.
6,265,546 B1 *  7/2001  Cohen et al. ................. 530/350

FOREIGN PATENT DOCUMENTS

WO    WO 00/74658 A1    12/2000
WO    WO 2004/017945 A1  3/2004

OTHER PUBLICATIONS

Verma et al., Nature, vol. 389, 1997, pp. 239-242.*
Anderson, Nature, vol. 392, 1998, pp. 25-30.*
Juengst, Brit. Med. J., vol. 326, 2003, pp. 1410-1411.*
International Search Report dated Mar. 28, 2003.
Olbrich et al., "Cationic Solid-Lipid Nanoparticles Can Efficiently Bind and Transfect Plasmid DNA," *Journal of Controlled Release*, vol. 77, No. 3, Dec. 13, 2001, pp. 345-355.
Sabel B. A.,"Forschungsthemen und-ziele," *Otto Von Guericke Universitat*, XP002233638, Forschungsbericht 2001, p. 229.

* cited by examiner

*Primary Examiner*—James S Ketter
(74) *Attorney, Agent, or Firm*—Jenkins, Wilson, Taylor & Hunt, P.A.

(57) ABSTRACT

The invention relates to the use of DNA-loaded nanoparticles for a transfection of DNA into cells in vitro or in vivo.

39 Claims, No Drawings

US 7,402,573 B2

USE OF NANOPARTICLES FOR THE DNA ADMINISTRATION TO A TARGET ORGAN

RELATED APPLICATIONS

This application is a continuation of PCT patent application Ser. No. PCT/EP02/008434, filed Jul. 29, 2002, the disclosure of which is incorporated herein by reference in its entirety.

TECHNICAL FIELD

The present invention relates to the use of nanoparticles for a transfection of DNA into eucaryotic cells. The invention also relates to the DNA administration to a target organ in the human or animal body. In particular, the present invention relates to the use of nanoparticles for the administration of cancer treatment-related DNA to a tumor-affected target organ in the human or animal body as, for example, the brain in the case of brain tumors. The invention also relates to the use of nanoparticles for the manufacture of a medicament against tumors in a target organ in the human or animal body. The invention also relates to a method of target-focussed treatment of the human or animal body by an administration of DNA suitable for preventing and/or therapeutically treating cancers.

BACKGROUND ART

Nanoparticles as used in the present invention are particles made of a synthetic or natural polymer and having a diameter in the range of 1 to 1000 nm. It could be shown in the prior art that nanoparticles are suitable to bind (e. g. adsorb, absorb, encompass) natural or synthetic substances like drugs, medicaments, diagnostic agents, antisense oligonucleotides, proteins, plasmids etc.) and carry such substances to target organs in the human or animal body, like the brain, liver, kidneys etc. (WO 95/22963 and WO 98/56361). Particularly, it could be demonstrated that nanoparticles may be used for carrying medicaments for the treatment of cancers to a target organ including the brain. In other words: Medicaments which otherwise do not pass across the blood brain barrier (bbb) are enabled to do so by binding them to suitable nanoparticles (WO 00/74658).

In particular, it was found that nanoparticles made, by polymerization, of a monomer selected from the group consisting of methylmethacrylates, alkylcyano-acrylates, hydroxyethylmethacrylates, methacrylic acid, ethylene glycol dimethacrylate, acrylamide, N,N'-bismethylene acrylamide, 2-dimethylaminoethyl methacrylate, N,N-L-lysinediyltere-phthalate, polylactic acid, polylactic acid-polyglycolic acid-copolymers, polyanhydrates, poly-orthoesters, gelatin, albumin, desolvated macromolecules or carbohydrates, polystyrene, poly(vinylpyridine), polyacroleine and polyglutaraldehyde in the presence of a stabilizer allowing the passage of the blood brain barrier, said particles optionally being coated by a substance as Polysorbate® 80 (Polyoxyethylene (20) sorbitan monooleate=Tween® 80) or the like, may be used to carry cancer treatment drugs like doxorubicine to a specific target organ like the brain (by passing accross the blood brain barrier) while other organs are not affected by said drug.

The transfection of genes or DNA, respectively, into cells in vivo with microparticles is described in the U.S. Pat. No. 6,248,720. The microparticles consisting of bioadhesive polymers, which are defined as polymers having the capability to bind to mucosal epithelium under normal physiological conditions, are administered orally or by inhalation and contain genes under the control of a promoter. The gene delivered may then be used for gene-therapeutic methods to be effected within the cell. This approach, however, could not be transformed into a practically useful method for transfecting genes into all kinds of cells, particularly due to the fact that the gene or DNA, respectively, transported by the microparticle could not pass across physiological barriers like the blood brain barrier. In accordance therewith, the above U.S. patent teaches only the unspecific gene therapy for the treatment of epithelial cells, gut-associated lymphatic cells, spleen cells or liver cells.

On a worldwide basis, tumors of the brain belong to the widespread tumors observed for young people. In the United States, 180,000 new cases of different brain tumors are found to occur, in particular tumors of the heterogeneous group of malign gliomas, which covers anaplastic astrocytomes, glioblastomes and, especially, the highly malign glioblastoma multiforme. The fact that preparations for pharmacologically suppressing the formation of recidives are not yet available, results into a high mortality of young people affected by such tumors. It is, hence, highly desired to find methods of successful treatment of such tumors in order to obtain an improvement of the rate of a successful treatment.

Malign gliomas and glioblastomes in humans are, in most cases, treated by surgical removal of the tumor tissue, followed by chemotherapy and/or irradiation. In many of the cases, the chemotherapy treatment is not satisfactory, since there are two barriers to overcome for cytostatic agents in the treatment step before having full effect, i. e. the blood brain barrier and a frequently occurring intrinsic chemoresistance of the blood brain barrier and of the tumor. Hence, it is essential in the course of the pharmacological treatment of brain tumors of the above kind to develop strategies for a transport of said chemotherapeutic agents across the blood brain barrier in vivo. Among the known methods are methods of opening the brain (invasive treatment) for opening the blood brain barrier, methods of modifying the pharmacological agent, whereby the modification enables the agent to pass across the blood brain barrier, and methods of using chimeric peptides for targeting small pharmacologically effective molecules to specific sites within the brain.

In the above-referenced WO publications, inter alia, proposals were made for drug delivery systems allowing the targeting of drugs including anti-cancer drugs to specific organs in the human or animal body, and in particular to the brain whereby drugs which are known not to pass the blood brain barrier could be transported into the brain in order to treat brain cancers. Particularly, after coating nanoparticles loaded with an analgetic drug (e. g. the hexapeptide-encephaline, dalargine) or with an anti-cancer drug (e. g. doxorubicine) with Polysorbate® 80 and administering such pharmacological nanoparticle-containing compositions in a suitable vehicle to the human or animal body, an increased concentration of said drugs in the brain could be determined, compared to the case of an administration of said drugs alone, but without the nanoparticle drug delivery system.

Most approaches to deliver genes to cells make use of viruses or viral vectors into which genes or plasmids are inserted. Cells or tissue of the body is then exposed to the virus or viral vector containing the gene or plasmid. The virus then infects or enters into the cell and liberates the gene or plasmid into the interior of the cell. Ideally, the gene is then transcribed within the cell, and the resulting transcription products are biologically active. However, the approach using viruses or viral vectors has numerous problems, one of them being that viral vectors may produce toxic side effects. In addition, they provoke an immune response which is undesirable. Furthermore, a continuously expressing gene can be "switched off" by the cellular response and, thus, become inactive in a process of tolerance. Finally, viral vectors, due to their unspecific distribution within the body, do not allow a targeting of genes/DNA to specific sites within the body, particularly no targeting to areas protected by natural barriers as the blood brain barrier.

SUMMARY OF THE INVENTION

It was an object of the present invention to apply the approach of transporting cancer treatment drugs and DNA across the blood brain barrier to further substances effective in the treatment of cancers, particular of gliomas and glioblastomas. It was a further object of the invention to use nanoparticles for targeting new cancer treatment-effective agents and drugs to specific areas of the human or animal body and, particularly, for passing such drugs and agents across the blood brain barrier. It was a further object of the invention to propose a means for a more effective and less expensive transfection of DNA molecules into cells in vitro. It was a further object of the invention to include into the gene to be expressed an inducible promoter controlling the expression of the gene in the cell into which they are transfected.

It was now surprisingly found that not only the above (and many other) drugs may be transported across the blood brain barrier by means of suitably coated nanoparticles, but also macromolecules like genes suppressing the cancer activity may be bound to (or incorporated into) suitable nanoparticles and then may readily be transported across the blood brain barrier for an effective cancer activity suppression controlled by a specific promoter simultaneously transported. It was also surprisingly found that nanoparticles are a very effective and inexpensive means for transfecting DNA molecules into eucaryotic cells in vitro on a non-viral delivery route. It was also surprising that the timing of gene expression can be controlled so that the toxic effects induced by gene expression can be reduced and the probability can be lowered that cells become resistant to the gene product.

Hence, the present invention relates to the use of gene-loaded nanoparticles for a transfection of DNA into cells in vitro and in vivo, preferably into eucaryotic cells, more preferably into the brain, and most preferably into the brain of patients suffering from brain cancer.

Besides the brain use of the gene-loaded nanoparticles may also be made in other organs of the mammalian body affected by tumors. To give only a few examples, such other organs may be the liver, the kidneys, the intestine, the stomach, the lungs and the testicles.

The invention also relates to a process of administration of DNA to a target organ in the human or animal body, which process comprises
   preparing nanoparticles on a per se known synthesis route;
   loading said nanoparticles with DNA;
   administering said DNA-loaded nanoparticles to the human or animal body in an amount sufficient to obtain an effective DNA concentration in the target organ.

The invention also concerns the use of nanoparticles obtained by a process described in detail below for the administration of DNA to a target organ in a human or animal body.

The invention also relates to the use of nanoparticles obtained by a process described in detail below for the manufacture of a medicament against tumors in a target organ of the human or animal body.

The invention finally also relates to a method of target-focussed treatment of the human or animal body to prevent and/or therapeutically treat cancer, which method comprises administering to the body an effective amount of one or more than one DNA effective against cancer, said DNA being administered in a form combined with nanoparticles.

DETAILED DESCRIPTION OF THE INVENTION

The term "nanoparticles" as used herein denotes a carrier structure which is biocompatible and sufficiently resistant to chemical and/or physical destruction by the environment of use such that a sufficient amount of the nanoparticles remain substantially intact after entry into the human or animal body following intraperitoneal or oral or intraveneous administration so as to be able to reach the desired target organ, e. g. the brain, the liver, the kidneys etc. Usually, nanoparticles are solid colloidal particles. Drugs or other relevant materials (e. g. those used for diagnostic purposes in nuclear medicine or in radiation therapy and/or those used for preventive and/or therapeutic purposes) can be dissolved within the nanoparticles, entrapped, encapsulated and/or adsorbed or attached.

The nanoparticles are synthetic particles made of a natural or synthetic polymeric material. The particles have a diameter of below 1,000 nm, preferably between about 1 to 1,000 nm.

In the process and use of the present invention, the nanoparticles preferably comprise a polymeric material which is selected from the group consisting of polyacrylates, polymethacrylates, polyalkylcyanoacrylates, preferably polybutylcyanoacrylates, polyaryl-amides, polylactates, polyglycolates, poly-anhydrates, polyorthoesters, gelatin, polysaccharides, albumin, polystyrenes, polyvinyls, polyacrolein, polyglutaraldehydes and derivatives, copolymers and mixtures thereof. Monomer materials particulary suitable to fabricate biodegradable nanoparticles by emulsion polymerization in a continuous aqueous phase include acrylates, methacrylates (preferably methylmethacrylates), alkylcyanoacrylates (preferably butylcyanoacrylates), hydroxyethylmethacrylates, methacrylic acid, alkylene glycol diacrylates or dimethacrylates (preferably ethylene glycol dimethacrylate), acrylamide, N,N'-bismethylene acrylamide and 2-dimethylaminoethyl methacrylate. Other nanoparticles are made by different techniques from N,N-L-lysinediyl-terephthalate, alkylcyanoacrylate, polylactic acid, polylactic acid-polyglycolic acid-copolymers, polyanhydrates, polyorthoesters, gelatin, albumin, and desolvated macromolecules or carbohydrates. Further, also non-biodegradable materials can be used such as polystyrene, poly(vinylpyridine), polyacroleine and polyglutaraldehyde. A summary of materials and fabrication methods has been published (see J. Kreuter, (1991) Nanoparticles-preparation and applications. In: M. Donbrow (Ed.) *Microcapsules and nanoparticles in medicine and pharmacy.* CRC Press, Boca Ranton, Fla., pp. 125 to 141). The polymeric materials which are formed from monomeric and/or oligomeric precursors in the polymerization/nanoparticle generation step, are per se known from the prior art, as are also the molecular weights and molecular weight distribution of the polymeric material which a person skilled in the field of manufacturing nanoparticles may suitably select in accordance with the usual skill. Reference is, in this respect, made to Kreuter et al., loc. cit., and the references cited therein.

The term "DNA" as used in the present specification and claims basically refers to any DNA conceivable in the present field of the art. In preferred embodiments, the term "DNA" is meant to comprise two types of DNA, i. e. plasmid DNA, more preferably plasmid DNA comprising the information of tumor suppressor genes, even more preferably plasmid DNA comprising the information of the tumor suppressor genes p53 and pRB, on the one hand, and antisense oligonucleotides, more preferably antisense oligonucleotides against oncogenes, even more preferably antisense oligonucleotides against oncogenes like Bc12, on the other hand. There may be used one type of DNA (and, consequently, one type of DNA-loaded nanoparticles) in the present invention. Alternatively, two or more types of DNA may be used, resulting into a plurality of types nanoparticles loaded with different types of DNA and useable in accordance with the present invention.

Surprisingly, DNA and particularly DNA of the above two types could be incorporated into or adsorbed onto nanoparticles, and the two resulting DNA-nanoparticle complexes could be inoculated into the organism, particularly into the organism suffering from cancer (specifically, but not limited to, brain cancer). Thereafter, a suppression of the tumor proliferation could be observed, and even a tumor necrosis and apoptosis could be induced.

In a preferred, but not essential embodiment of the invention, plasmid DNA comprising a promoter, more preferably plasmid DNA comprising an inducible promoter, can be incorporated into the nanoparticles. By the novel step to include, into the DNA loaded to or into the nanoparticle and to be expressed within the cell, an inducible promoter, an external control of the expression of the relevant gene may be achieved, and the gene may be "switched" on and off at will. As an unexpected advantage over the prior art, the timing of the gene/DNA expression can be controlled. Such a control may reduce toxic side effects of a continuous gene expression and/or may lower the probability that cells become resistant to the gene products, producing a negative selection.

In a preferred embodiment of the invention, the human papilloma virus upstream regulatory region (HPV-URR) was used as the inducible promoter. The expression of the tumor suppressor is induced after the administration of Dexamethasone or other inducers or compounds. On that way, an apoptosis of the tumor cells as well as a regression of the tumor could be achieved.

Furthermore, strong effects including a tumor regression could be achieved by a combination administration of one or more than one type(s) of DNA-containing nanoparticles and nanoparticles containing one or more than one cytostatically effective substance(s). In a preferred embodiment, tumor suppressor DNA, even more preferred: behind an inducible promoter, may be injected prior to inoculation of a nanoparticle complex containing a cytostatically effective compound. In an even more preferred embodiment of the combination administration, the cytostatically effective compound is Doxorubicine.

In the process of transfection of DNA into cells, and in the process of administration of a DNA to a target organ in the human or animal body as well, the first step comprises the preparation of nanoparticles on a per se known synthesis route. Each synthesis route suitable for preparing nanoparticles suitable for a DNA administration may basically be used. In a preferred embodiment of the process, the synthesis starts from one of the monomeric materials being the chemical basis for the polymers mentioned above. The monomeric material, or optionally more than one of the monomer materials mentioned above, is/are polymerized, preferably in a step of interfacial polymerization, in a suitable non-solvent for the nanoparticles generated. As usual and in detail described in the prior art referred to above, the polymerization is conducted in the presence of a suitable stabilizer at temperatures and in concentrations known to a person skilled in this field of the art, e. g. from the above references.

In preferred embodiment of the invention, the process of preparing the nanoparticles may comprise the step of including a stabilizer into the nanoparticles. Hence, in such a case, the stabilizer must be an essential component of the composition for preparing the nanoparticles. A stabilizer may preferably be a compound having surfactant properties.

In preferred embodiments, only one stabilizer is used. In this case, the transport of the DNA to a specific target within or on the human or animal body can be achieved in an ideal manner. For example, a DNA can be brought to and allowed to pass across the blood brain barrier (bbb) in a very effective manner so that the amount of effective substance at the site of effect is considerably enhanced, and the dose administered to the human or animal can be reduced correspondingly. However, it is also possible to use more than one, e. g. two or more, stabilizer(s).

Basically, each stabilizer allowing to achieve the object of the present invention is suitable to be incorporated into the drug targeting system of the invention.

In preferred embodiments of the invention, said stabilizer for the nanoparticles being used for a transfection of DNA into cells of for an administration of DNA in a targeted manner is selected from the group consisting of stabilizers which allow a prevention of nanoparticle agglomeration. More specifically, the stabilizer may be selected from compounds enhancing the bond between the DNA and the nanoparticles.

In specifically advantageous processes of preparing the nanoparticles, said stabilizer comprises a substance selected from the group consisting of polysorbates, preferably polysorbate 80, polysorbate 85, polysorbate 81; dextrans and derivatives thereof, preferably dextran 12.000, dextran 70.000, Diethylaminoethyl-(DEAE-) dextran, carboxylic acid esters of multifunctional alcohols, poloxameres, poloxamines, alkoxylated ethers, alkoxylated esters, alkoxylated mono-, di and triglycerides, alkoxylated phenoles and diphenoles, substances of the Genapol® and Bauki® series, metal salts of carboxylic acids, metal salts of alcohol sulfates and metal salts of sulfosuccinates and mixtures of two or more of said substances. For example, said stabilizer comprises a substance selected from the group consisting of polysorbate 80, polysorbate 85, polysorbate 81, dextran 12.000, dextran 70.000, DEAE-dextran, carboxylic acid esters and preferably fatty acid esters of glycerol and sorbitol, even more preferably glycerol monostearate, sorbitan monostearate and sorbitan monooleate, poloxamer 188 (Pluronic® F68), ethoxylated ethers, ethoxylated esters, ethoxylated triglycerides, ethoxylated phenoles and diphenoles, metal salts of fatty acids and metal salts of fatty alcohol sulfates, preferably sodium salts of fatty acids and of fatty alcohol sulfates, even more preferably sodium stearate and sodium lauryl sulfate and mixtures of two or more of said substances.

In the process of the invention, it has turned out that the nanoparticles yield especially good results, if the stabilizer of the nanoparticles used in the preparation process comprises a substance selected from DEAE-dextran and mixtures thereof with other stabilizers as mentioned above. When using such nanoparticles, the step of targeting the physiologically effective substance(s) to a specific site within or on the human or animal body could be very well accomplished. In particular, in the step of targeting DNA to the blood brain barrier and penetrating said substance(s) across the bbb without an agglomeration of the particles, a relatively high effective amount of the DNA in the brain available for action on the tumor was found. Thus, the efficiency of passage of said substance across the bbb could be enhanced, while the amount of nanoparticles could particularly be reduced if the nanoparticles contained DEAE dextran as the stabilizer, optionally in admixture with other stabilizers.

In a preferred embodiment of the invention, the process of preparing the nanoparticles may comprise the step of applying a coating to the nanoparticles in order to allow that the DNA may readily be transported to the target organ and/or pass across the blood brain barrier. Basically, all coatings described in the prior art for allowing nanoparticles and/or their drug components to pass the blood brain barrier may be used also in the present invention. One substance may be used as the coating, or a plurality of substances (two, three etc. substances) may be used as the coating material. In a preferred embodiment, the coating may comprise or consist of Polysorbate 80 (commercially available as Tween® 80 from ICI). Polysorbate 80 may be used alone or in combination with other suitable coating materials, as, for example with Poloxamers (commercially available as Pluronic® from BASF Wyandotte). The amounts of coating material used in the preparation of the nanoparticles may easily be selected by a skilled person in accordance with the amounts of coating used in the prior art. In a particularly preferred embodiment, the amount of coating material, when preparing nanoparticles in accordance with the process of the present invention, is in a range of 0.1 to 100 mg/ml coating solution, more preferably in a range of 1 to 50 mg/ml, even more preferred in a range of 5 to 20 mg/ml, for example 10 mg/ml.

The third step of the transfection process of the present invention comprises the step that the DNA-loaded nanoparticle is incubated with the culture of cells, to which the DNA is to be transfected. In a preferred embodiment of the invention, this is performed in a usual culture medium, and more preferably for a time sufficient to allow the DNA to be transfected into the cells. The time (as also other conditions of the reaction) may be selected freely by a person skilled in this field of the art without any restriction, particularly, the reaction conditions may be determined within one or two orienting test experiments. In more preferred embodiments, the time for incubating the DNA-loaded nanoparticles with the cells in culture is within a range of from 1 h to 72 h, even more preferred within a range of from 6 h to 36 h, and most preferred within a time of from 12 h to 30 h, for example 24 h. The concentration of DNA-loaded nanoparticles in the culture medium for the transfection step preferably is in a range of from 1 µg to 20 µg, even more preferred within a range of from 1 µg to 10 µg, for example from 1 µg to 6 µg. The temperatures are usual culturing temperatures for cells and may preferably be within a range of 20 to 40° C., more preferably in the range of from 30 to 37° C. In specific embodiments of the invention, there may be used only one culture medium. It is, however, within the experience and knowledge of a person skilled in the present field that there may be used different culture media in the course of the transfection procedure. For example, in the use of the present invention, it is preferred that the nanoparticle DNA complex is added to the normal culture medium which is for example Modified Eagles Medium (MEM) or Dulbeccos Modified Eagles Medium (D-MEM), and the nanoparticles loaded with DNA are incubated with the cells in said culture for a certain time, for example 5 h. Five hours post addition, the culture medium is changed, preferably to fresh medium, even more preferred to fresh medium of the same type, and the cells are cultured for another period of time, for example for another 24 h, at normal conditions, for example (without restriction) at 37° C. in a humidified atmosphere containing 5% $CO_2$. The determination of a successful transfection of the DNA into the cells can be carried out on usual ways, preferred routes of which are a visualization of the expression of reporter genes after fixation of the cells by chemical reaction or by fluorescence. Furthermore, the transcription of other genes is analyzed by, for example, the Northern Blot technique.

The third step of the administration process of the present invention is the administration of the DNA-loaded nanoparticles, prepared and loaded in the two previous steps as described above, to the human or animal body in an amount sufficient to obtain an effective DNA concentration in a target organ.

The administration may be performed on each suitable route. For example, the DNA-loaded nanoparticles may be administered on the oral, subcutaneous, intraveneous, or intraperitoneal routes, and the intraveneous or intraperitoneal routes are particularly preferred. Also a combination of more than one of the afore-mentioned routes is possible in specific embodiments of the invention. The DNA is transported to the target organ, carried by the nanoparticles, wherein the process of the invention particularly achieves a targeting of the DNA to specific organs, while others will not be provided with the DNA. This allows the reduction of the dose of DNA-loaded nanoparticles and simultaneously allows the prevention of side effects at other sites of the human or animal body.

In any case, the DNA concentration obtained at the specific target organ must be a concentration effective in the treatment of cancer.

In a particularly preferred embodiment, it could be learnt that, in order to obtain the above concentration in the target organ, the amount of DNA-loaded nanoparticles per dosage unit should be in the range of 5 mg to 20 mg, based on 1 kg of body weight of the human or animal to be treated. 1 to 4 dosage units, preferably 1 to 3 dosage units, should be administered per day in order to obtain the desired anti-cancer effect in the target organ.

In accordance with the present invention, the nanoparticles loaded with DNA preferably selected from the group consisting of plasmid DNAs and antisense oligonucleotides can be used for an effective treatment of cancers, particularly if the target organ is the brain. Other target organs may be the liver, the kidneys, the intestine, the stomach, the lungs and the testicles. After using the DNA-loaded nanoparticles, the effective DNA concentration at the target organ could be enhanced considerably, compared to the case of administration of DNA not loaded on nanoparticles. Particularly in cases where the administration of DNA-loaded nanoparticles is combined with the administration of nanoparticles loaded with an anticancer medicament/cytostatically effective substance, an apoptosis of the tumor cells and a substantial tumor regression could be achieved.

The invention also relates to the use of nanoparticles loaded with DNA for the administration of DNA to a target organ within the human or animal body. Such a use may be a use where the nanoparticles are loaded with DNA (one DNA or a plurality of DNAs) alone or a use where the nanoparticles are loaded with DNA (one DNA or a plurality of DNAs) comprising an inducible promoter. In the latter case, the DNA (s) comprising an inducible promoter may be administered to the body by means of the nanoparticles. In a preferred embodiment, the DNA is one type of DNA or is more than one type of DNA, e. g. two types of DNA which are loaded onto the same type of nanoparticles or on different types of nanoparticles so as to result into one type or two different types of DNA-loaded nanoparticles. In preferred embodiments of such a use, the DNA is DNA related to a cancer treatment and more preferably is selected from the group consisting of plasmid DNAs and antisense oligonucleotides, preferably from the group consisting of plasmid DNAs comprising the information of tumor suppressor genes and antisense oligonucleotides against oncogenes. In an even more preferred embodiment, the DNA is selected from plasmid DNA comprising the information of the tumor suppressor genes p53 and pRB and antisense oligonucleotides against oncogenes like Bcl2 or Tgfβ.

The invention further relates to the use of nanoparticles loaded with DNA for the manufacture of a medicament against tumors in a target organ of the human or animal body. Such a use may be a use where the nanoparticles are loaded with DNA (one DNA or a plurality of DNAs) alone or a use where the nanoparticles are loaded with DNA (one DNA or a plurality of DNAs) comprising an inducible promoter for said DNA(s). In the latter case, the DNA(s) comprising an inducible propoter may be used for the manufacture of a medicament. The target organ addressed may preferably be the brain. In other embodiments, the target organs my be one or more organs selected from the group consisting of the brain, the liver, the kidneys, the intestine, the stomach, the lungs and the testicles. In a preferred embodiment, the DNA is one type of DNA or is more than one type of DNA, e. g. two types of DNA which are loaded onto the same type of nanoparticles or on different types of nanoparticles so as to result into one type or two different types of DNA-loaded nanoparticles. In preferred embodiments of such a use, the DNA is DNA related to the treatment of cancer and, even more preferably, is selected from the group consisting of plasmid DNAs and antisense oligonucleotides, preferably from the group consisting of plasmid DNAs comprising the information of tumor suppressor genes and antisense oligonucleotides against oncogenes. In an even more preferred embodiment, the DNA is selected from plasmid DNA comprising the information of the tumor suppressor genes p53 and pRB and antisense oligonucleotides against oncogenes like Bcl2 or Tgfβ. Such medicaments based on nanoparticles may be of immense advantage over usual anticancer drugs and chemical substances since they may easily be administered to a patient, or a patient may himself take the medicaments without the risks which prevent, up to now, a self-medication in cases of cancer. In addition, as pointed out above, such medicaments may be combined with nanoparticles loaded with anticancer medicaments and, particularly, cytostatically effective agents. By such combinations, an even more effective treatment of otherwise untreatable tumors may be effected.

Particularly, with the DNA-loaded nanoparticles used in the field of the present invention, DNA related to the treatment of cancer, optionally in combination with other cancer treatment-related medicaments and agents, can be targeted to a specific organ in the human or animal body, specifically to a tumor-affected organ. In a particularly preferred embodiment, the tumor-affected organ is the brain, and the administration of the nanoparticles having adsorbed thereto or absorbed thereon or included therein one or more than one DNA allows a passage of said DNA across the blood brain barrier. Particularly, the targeted treatment of malign carcinomas like malign gliomas, anaplastic astrocytomes, glioblastomes and, particularly, of the glioblastoma multiforme, is possible.

The DNA-loaded nanoparticles used in the present invention are also useable in the gene-therapeutic treatment of hereditary diseases. Examples of such hereditary diseases are adrenogenital sydrome (AGS), alpha-1-antitrypsin defect, APC resistance type leiden, chorea huntington, cystic fibrosis, factor V leiden mutation, fragile X-syndrome, gaucher syndrome, hemochromatosis, homocystinuria, hypercholesterinemia, hyperlipidemia type III, isolated lissencephalitis-sequence, cri-du-chat syndrome, lesch-nyhan syndrome, lissencephalitis, miller-dieker syndrome, morbus osler, morbus fabry, mucoviszidosis, musculodystrophia, phenylketonuria, prothrombin mutation, retinoblastoma and walker-warburg syndrome.

Summarizing the advantages, the DNA-loaded nanoparticles used according to the invention may readily be available in the specific anti-cancer therapy due to their property that they are specifically targeted to a target organ in the human or animal body without affecting other organs. This allows a reduction of the administration of cytostatically effective agents. In combination with those, the—otherwise deleterious and side—effect affording dose of cytostatics may considerably be reduced.

The following examples illustrate the invention even more. The examples relate to preferred embodiments only and should not be construed to limit the invention.

EXAMPLES

Example 1

DNA-loading by adsorption onto nanoparticles could be effected on the following way: 10 mg of lyophilized PBCA-(DEAE-dextran) nanoparticles were prepared by polymerizing, on a usual route for the manufacture of nanoparticles, butylcyanoacrylate to the corresponding polymer (polybutyl cyanoacrylate=PBCA) having an average molecular weight of about 1,547 g/mole and containing Dextran 70.000 and diethylaminoethyl dextran (DEAE-dextran) in a molar ratio of 1.5 to 1 as the stabilizer. The nanoparticles having an average diameter of about 200 to 300 nm were resuspended in 1 ml of a phosphate buffer solution having a pH of 4.5 to 5.5 with stirring. 20 to 150 μg/ml DNA (plasmid DNA comprising the information of the tumor suppressor gene p53) in phosphate buffer (or, alternatively, in $H_2O$) was added to the suspension, while stirring was continued for 4 to 16 h. After centrifugation of the mixture, the supernatant was analyzed by UV spectroscopy. The pellet of DNA-loaded nanoparticles was recovered and re-suspended in 1 ml of millipore-filtered water. 10 mg of Tween® 80 were added to the suspension in order to provide a coating on the nanoparticles. The suspension was stirred for 30 min, followed by centrifugation to remove unbound coating component. The resulting pellet was again re-suspended in 1 ml of 0.9% NaCl solution; the thus obtained suspension was ready for injection.

Example 2

For a transfection of DNA into cells in vitro, a DNA nanoparticle complex (plasmid DNA comprising the information of the tumor suppressor gene p53) was added to cells cultured in D-MEM (Dulbecco's modified Eagles medium). 5 h after addition of the DNA nanoparticle complex the medium was changed (to fresh D-MEM) and was further incubated at 37° C. for 24 h. An expression of the reported genes (reporter=β-galactosidase, green light protein, following a heterologous promotor) was visualized after fixation of the cells by chemical reaction or fluorescence. Transcription of other genes was analyzed by Northern Blot analysis.

Example 3

The efficiency of nanoparticles loaded with reporter genes (reporter=β-galactosidase, green light protein, following a heterologous promotor) was further analyzed in a model test with rats. Rats of the strain CD Fisher were inoculated intracranially with cells of the glioma cell lines C6, F98 or RG2 the latter ones resulting into a more rapid growth of tumors.

Male Fisher CD rats (age: 15 weeks, 250 g) were narcotized with Ketanest (80 mg/kg, i.p.) and then Rompun (12.5 mg/kg i.m.). The head was then fixed in a stereotactic apparatus and was then opened (3 to 4 mm lateral, right side close to the bregma, diameter of the hole, 1 mm) by means of a high speed drill. By means of a 26 G needle connected to a Hamilton micro-syringe, $1 \times 10^3$ tumor cells suspended in serum-free medium (3 µl) were inoculated into a depth of 4 mm into the brain. The suture was closed by means of clamps.

In a histological test, the distribution of the DNA-loaded nanoparticles was determined by administering systemically to the animals a suspension of reporter gene-loaded DNA-nanoparticle complex in an amount of 5 mg/500 µl (the volume injected was 500 µl). A perfusion was performed after 24 h and after 5 days. Unstained cryostat sliced cuts of all organs served for determining the localization of fluorescent particles by observing the slices with a fluorescence microscope. The exact localization was determined with parallel slices stained with methylene blue. Reporter gene expression was found in the brain, the liver, the spleen, the kidneys and the gut, most dominant in the brain tumor tissue.

What is claimed is:

1. A method for transfecting DNA into cells in vivo, the method comprising contacting the cells with a polyalkylcyanoacrylate nanoparticle loaded with the DNA, whereby the DNA enters the cells.

2. A method for administering DNA to a target organ in a subject, the method comprising:
   (a) preparing polyalkylcyanoacrylate nanoparticles by polymerizing one or more alkylcyanoacrylates;
   (b) loading said polyalkylcyanoacrylate nanoparticles with DNA; and
   (c) administering said DNA-loaded polyalkylcyanoacrylate nanoparticles to the subject in an amount sufficient to obtain an effective concentration of the DNA in the target organ.

3. The method of claim 2, wherein the administering further comprises administering nanoparticles loaded with an anti-cancer medicament.

4. The method of claim 2, wherein the polymerizing step employs a stabilizer.

5. The method of claim 2, wherein the polyalkylcyanoacrylate nanoparticles comprise a coating.

6. The method of claim 2, wherein the DNA encodes a tumor suppressor polypeptide or comprises an antisense oligonucleotide directed against an oncogene.

7. The method of claim 2, further comprising loading said polyalkylcyanoacrylate nanoparticles with a nucleotide sequence comprising an inducible promoter.

8. The method of claim 2, wherein the administering step is by oral, intraperitoneal, or intravenous administration, or a combination thereof.

9. The method of claim 2, wherein the administering provides a DNA concentration in the target organ that is effective for treatment of cancer or for treatment of a hereditary disease.

10. The method of claim 2, wherein an amount of DNA-loaded polyalkylcyanoacrylate nanoparticles administered per dosage unit is in the range of from 5 to 20 mg/kg body weight of the subject.

11. The method of claim 2, wherein the administering comprised administering 1 to 4 dosage units per day.

12. The method of claim 2, further comprising administering to the subject at least one additional nanoparticle loaded with an anti-cancer medicament or a cytostatically effective agent.

13. A method for administering DNA to a target organ in a human or animal body, the method comprising contacting the target organ with a polyalkylcyanoacrylate nanoparticle loaded with DNA, whereby the DNA enters one or more cells of the target organ.

14. The method according to claim 13, wherein the DNA comprises an inducible promoter operatively linked to a nucleotide sequence.

15. A method for suppressing tumor cell proliferation, the method comprising contacting a tumor cell with a DNA-loaded polyalkylcyanoacrylate nanoparticle, whereby the DNA enters the tumor cell and suppresses proliferation of the tumor cell.

16. The method according to claim 15, wherein the DNA comprises an inducible promoter operatively linked to a nucleotide sequence, the expression of which in the tumor cell suppresses proliferation of the tumor cell.

17. The method according to claim 13, wherein the nucleotide sequence encodes a tumor suppressor polypeptide or comprises an antisense oligonucleotide directed against an oncogene.

18. The method according to claim 16, wherein the promoter comprises a human papilloma virus upstream regulatory region (HPV-URR).

19. The method according to claim 13, wherein the target organ is a tumor-affected target organ.

20. The method according to claim 13, wherein the target organ is selected from the group consisting of brain, liver, kidney, intestine, stomach, lung, and testicle.

21. The method according to claim 13, wherein the tumor is selected from the group consisting of a malignant glioma, an anaplastic astrocytoma, a glioblastomas, and a glioblastoma multiforme.

22. A method of target-focused treatment of a human or an animal to prevent and/or therapeutically treat cancer, the method comprising administering to the human or the animal an effective amount of one or more DNA sequences effective against cancer or encoding a polypeptide effective against cancer, wherein said DNA sequences are loaded onto one or more polyalkylcyanoacrylate nanoparticles.

23. The method of claim 22, wherein said one or more DNA sequences are operatively linked to an inducible promoter.

24. The method of claim 22, wherein the cancer is selected from the group consisting of a malign glioma, an anaplastic astrocytoma, a glioblastoma, and a glioblastoma multiforme.

25. The method of claim 22, wherein the administering is by oral, intraperitoneal or intravenous administration, or a combination thereof.

26. The method of claim 22, wherein the DNA is adsorbed to, absorbed on, or present within the polyalkylcyanoacrylate nanoparticles.

27. The method of claim 22, wherein the polyalkylcyanoacrylate nanoparticles further comprise at least one of a stabilizer and a coating.

28. The method of claim 27, wherein the stabilizer is selected from the group consisting of stabilizers allowing a prevention of nanoparticle agglomeration and stabilizers enhancing the bond between the one or more DNA sequences and the nanoparticles.

29. The method of claim 27, wherein the polyalkylcyanoacrylate nanoparticles comprise a coating comprising a substance selected from the group consisting of a polysorbate, a poloxamer, and a polyethylene glycol.

30. The method of claim 3, further comprising administering a cytostatically effective agent.

31. The method of claim 2, wherein the polyalkylcyanoacrylate nanoparticles comprise polybutylcyanoacrylate nanoparticles.

32. The method of claim 4, wherein the stabilizer is diethylaminoethyl dextran.

33. The method of claim 5, wherein the coating comprises a surfactant.

34. The method of claim 33, wherein the surfactant comprises polyoxyethylene (20) sorbitan monooleate.

35. The method of claim 11, wherein the administering comprised administering 1 to 3 dosage units per day.

36. The method according to claim 20, wherein the target organ is brain.

37. The method according to claim 28, wherein the stabilizer is selected from the group consisting of polysorbate 80, polysorbate 81, polysorbate 85, dextran 12,000, dextran 70,000, diethylaminoethyl dextran (DEAE dextran), a fatty acid ester of glycerol and sorbitol, poloxamer 188, an ethoxylated ether, an ethoxylated ester, an ethoxylated phenol, an ethoxylated diphenol, a metal salt of a fatty acid, an metal salt of a fatty alcohol sulfate, and combinations thereof.

38. The method according to claim 37, wherein the metal salt comprises a sodium salt.

39. The method of claim 29, wherein the polysorbate comprises polyoxyethylene (20) sorbitan monooleate.

* * * * *